United States Patent [19]

Harpster

[11] Patent Number: 5,485,754
[45] Date of Patent: Jan. 23, 1996

[54] APPARATUS AND METHOD FOR MEASURING THE AIR FLOW COMPONENT AND WATER VAPOR COMPONENT OF AIR/WATER VAPOR STREAMS FLOWING UNDER VACUUM

[75] Inventor: Joseph W. Harpster, Galena, Ohio

[73] Assignee: Intek, Inc., Westerville, Ohio

[21] Appl. No.: 230,974

[22] Filed: Apr. 21, 1994

[51] Int. Cl.$^6$ .................................................. G01F 1/74
[52] U.S. Cl. ................................................. 73/861.04
[58] Field of Search ........................... 73/861.02, 861.03, 73/861.04

[56] References Cited

U.S. PATENT DOCUMENTS

| | | | |
|---|---|---|---|
| 3,898,882 | 8/1975 | Prokopius | 73/861.04 |
| 4,739,647 | 4/1988 | Monticelli Jr. | 73/861.04 X |
| 4,932,788 | 6/1990 | Yeh | 73/861.04 X |
| 5,190,726 | 3/1993 | Shinoki | 73/861.04 X |
| 5,343,760 | 9/1994 | Sultan et al. | 73/861.04 |

*Primary Examiner*—Richard Chilcot
*Assistant Examiner*—William Oen
*Attorney, Agent, or Firm*—Mueller and Smith

[57] ABSTRACT

The inventive method for measuring the mass of the gas component and the mass of the water vapor component of a gas/water vapor source stream flowing in a conduit under reduced pressure comprises storing a correlation of relative saturation of water in said gas and the output electrical signal of a relative humidity sensor. Next, a correlation of the flow rate of the gas component of a flowing gas/water vapor reference stream and the output electrical signal of a temperature-compensated flow sensor as a function of water vapor density is stored. A correlation of maximum water vapor saturation in the gas as a function of temperature also is stored. An electrical signal of a temperature sensor in contact with said source stream then is generated. An output electrical signal of a relative humidity sensor in contact with said source stream also is generated. An output electrical signal of a temperature-compensated flow sensor in contact with said source stream further is generated. The relative humidity output signal is compared with said stored relative saturation correlation to derive a relative saturation value which value is multiplied by the maximum water vapor saturation correlation for the temperature determined from the temperature sensor signal in order to derive the mass density of the water vapor component of said source stream. Finally, the flow sensor signal is compared with said stored gas flow rate correlation at derived water vapor mass density to derive the flow rate of the gas component of said source stream. Also disclosed is the apparatus for carrying out the method. Also disclosed is a method and apparatus to incorporate a pressure sensor along with these three primary sensors to provide other correlations to provide redundancy to the relative humidity sensor in the event of its failure and to provide indications of the existence of water mist contamination of the source stream.

12 Claims, 4 Drawing Sheets

5,485,754

APPARATUS AND METHOD FOR MEASURING THE AIR FLOW COMPONENT AND WATER VAPOR COMPONENT OF AIR/WATER VAPOR STREAMS FLOWING UNDER VACUUM

BACKGROUND OF THE INVENTION

The present invention relates to the measurement of flow rates of gas/water vapor mixtures through conduit and more particularly to the measurement of the gas component and the water vapor component under vacuum flow conditions in the conduit.

The measurement of steam and water flow rates in steam power plants (both conventional and nuclear) is a required operation at a variety of junctures in the various steam and water circuits comprising the steam power plant. Referring to FIG. 1, steam produced within a boiler vessel 10 is taken through steam line 12 and applied to steam turbine 14. Exhaust steam 16 from turbine 14 is condensed in a condenser 18 and returned via line 20 and pump 22 to pressure vessel 10 via line 24 as feedwater. Cooling water is passed through a multiplicity of tube, such as tube 17, connected between headers 19 of condenser 18 via line 26 by pump 28. Finally, vacuum pump 30 maintains reduced pressure in condenser 18 via line 32 with line 34 vented to atmosphere. It is desirable to measure the flow rate of air that enters condenser 18 via leaks to this low pressure region and removed by pump 30, with flow sensor 36 located in line 32.

Over the years, industry has recognized the importance to minimize the back-pressure at the exhaust of the steam turbines where such low pressure condensers are employed. As exhaust pressure rises, more fuel is required to generate additional steam to maintain turbine output power. An increase in the back-pressure decreases plant operating efficiency. In the electrical power industry, millions of dollars per year per generating plant can be lost due to unnecessary rise in turbine exhaust pressure. A manageable cause for increased back-pressure is air leakage into the evacuated end of the turbine and its exhaust steam condenser.

To remove air and other non-condensable gases that enter the condenser space, a vacuum pump, air injector, or some other contrivance is employed. For systems most commonly employed, a line or conduit generally is installed between the condenser and the pump within which these gases are conveyed. They enter the air removal equipment generally at a pressure in the range of about 1 to 6 inches of mercury absolute where they are compressed to atmospheric pressure and released to the environment.

In addition to non-condensable gases passing through the conduit, an amount of water vapor is contained which generally is determined by the absolute pressure within the condenser and the temperature of cooling water passing through the condenser tubes. The partial pressure of the water vapor generally is related to the temperature of the cooling water. This pressure represents the minimum obtainable back pressure available to the turbine and generally is related to local environmental conditions. Pressures higher than this which are caused by air leaks require attention because this added pressure component can be diminished by maintenance procedures.

Flow instruments available on the market have limitations which preclude their use for measurement of air flow in the conduit at low pressure. The mass flow rate is below the low end sensitivity of most instruments. Further, the variable concentration of combined air and water vapor flow cannot properly be separated such that air only is measured.

The most common method of measuring air leaks is to physically observe the height of a float in a variable area flow meter or the pressure drop across an orifice in a differential pressure flow meter, either of which is connected to the exhaust end of the vacuum pump. In addition to being inconvenient, high inaccuracy is present using these methodologies. The air is contaminated with liquid water due, in part, to condensation of the pumped water vapor from the condenser being raised to atmospheric pressure and also from pump designs which use a water seal, both of which adds buoyancy to the float or partial closure of the orifice. Another limitation of these methodologies is that the measurement requires plant personnel to observe and record at intervals which is inconvenient and costly to the plant operator. Further, without an output signal that can be recorded in real time, the measurement cannot be correlated in time with other events which could be used to identify sources of leaks. Also, because of the measurement location, the measurement cannot be used to determine if the air flow results from a fault pump seal or an air leak into the condenser space.

BROAD STATEMENT OF THE INVENTION

The present invention broadly is addressed to a method, system, and apparatus for determining the amount of non condensable gas, e.g. air, flowing within a conduit under low pressure conditions in the presence of varying amounts of water vapor. Although the invention may find other applications such as, for example, the measurement of air flow in dryers operating at various absolute pressures as may be found, for example, in the food or paper industry processing, the invention will be described for the specific application of measuring non-condensable gas flow in the suction line of air removal equipment found in steam turbine power generating equipment (both nuclear and conventional fuel plants).

Although a principal element of the invention is a flow velocity sensing device, the invention includes the application, in vacuum, of a water vapor density sensor including temperature compensation which can be used to compensate the non-condensable gas flow sensor signal for the amount of water vapor content. Additionally, a pressure sensing device also is described as providing indication of distinctly different states of operation which may occur within the condenser and for determining the flow rate of the water vapor component. The pressure sensor signal also may be used for flow signal manipulation should the water vapor sensor become non-operational. The system employs proven flow, temperature, and pressure sensing devices along with common water vapor sensing devices found by testing to perform in a vacuum environment. As a consequence, a practical and low cost measuring apparatus is realized suitable for quantifying air leaks into the vacuum regions of steam turbines. The apparatus employs direct measurement of water vapor content in the flowing stream rather than relying on the assumption that equilibrium state physical laws are represented by indirect measurements as may be found in other systems.

The inventive method for measuring the mass of the gas component and the mass of the water vapor component of a gas/water vapor source stream flowing in a conduit under reduced pressure comprises storing a correlation of relative saturation of water in said gas and the output electrical signal of a relative humidity sensor. Next, a correlation of the flow rate of the gas component of a flowing gas/water vapor reference stream and the output electrical signal of a temperature-compensated flow sensor as a function of water vapor density is stored. A correlation of maximum water vapor saturation in the gas as a function of temperature also is stored. An electrical signal of a temperature sensor in contact with said source stream then is generated. An output electrical signal of a relative humidity sensor in contact with said source stream also is generated. An output electrical signal of a temperature-compensated flow sensor in contact with said source stream further is generated. An output electrical signal of a pressure sensor in contact with the source stream is generated. The relative humidity output signal is compared with said stored relative saturation correlation to derive a relative saturation value which value is multiplied by the maximum water vapor saturation correlation for the temperature determined from the temperature sensor signal in order to derive the mass density of the water vapor component of said source stream. The flow sensor signal is compared with said stored gas flow rate correlation at derived water vapor mass density to derive the flow rate of the gas component of said source stream. Finally, the measured pressure, air mass flow rate, partial pressure water vapor as a function of water vapor density and conduit geometry are manipulated to obtain the water mass flow rate. Knowing these, the mass flow rate of the water vapor and air can be summed and by comparing these data with pump capacity curves, the plant operator also has a means by which pump degradation can be measured.

The inventive apparatus which implements the foregoing method comprises: (a) memory in which is stored the correlation of relative saturation of water in said gas and the output electrical signal of a relative humidity sensor; (b) memory in which is stored the correlation of the flow rate of the gas component of a flowing gas/water vapor reference stream and the output electrical signal of a temperature-compensated flow sensor as a function of water vapor density; (c) memory in which is stored a correlation of maximum water vapor saturation in the gas as a function of temperature; (d) a temperature sensor in thermal contact with the source stream which generates an electrical signal representative of the temperature of said source stream; (e) a relative humidity sensor in contact with said source stream which generates an electrical signal representative of the relative humidity in said source stream; (f) a temperature-compensated flow sensor in contact with said source stream which generates an electrical signal representative of the flow rate of said source stream; (g) a comparator which compares the signal from relative humidity sensor (e) with said stored correlation in memory (a) to derive a relative saturation value which value is multiplied by the maximum water vapor saturation correlation in memory (c) for the temperature determined from temperature sensor (d) in order to derive the mass density of the water vapor component of said source stream; and (h) a comparator which compares the electrical signal from flow sensor (f) with said stored correlation in memory (b) for the derived water vapor density (g) to derive the flow rate of the gas component of said source stream.

The relative humidity or water vapor sensor output signal is calibrated for determining the relative saturation of water vapor in a gas/water vapor mixture held under reduced pressure and various temperatures by the steps of: (a) in a gas/water vapor mixture of known composition which is less than saturation and which is held under reduced pressure and various temperatures, recording the electrical signal from a relative humidity sensor which signal corresponds to the known water vapor density; (b) determining the water vapor saturation density from known "properties of saturated steam" at said varying temperatures for a practical range of water temperatures held under reduced pressure; (c) at each temperature, dividing the known water vapor density from step (a) by the saturation water vapor density of step (b) to generate the relative water vapor saturation at varying temperatures and pressures; and (d) finally correlating the output electrical signal in step (a) to the relative saturation generated in step (c).

Advantages of the present invention include the recognition that conventional water vapor (relative humidity) sensors can be used in vacuum lines for the determination of mass density and relative saturation of water vapor in a flow under vacuum. Another advantage is the ability to separately determine both gas (air) flow rate and water vapor flow rate in a mixture flow under vacuum. A further advantage is that the inventive apparatus conveniently can be combined with a processor (computer) for additional capability and flexibility. These and other advantages will be readily apparent from the disclosure herein.

BRIEF DESCRIPTION OF THE DRAWINGS

FIG. 8 is a simplified perspective view of a water vapor sensor housed in a chamber for use when greater than 100% relative saturation or steam conditions are encountered.

Figure 1:
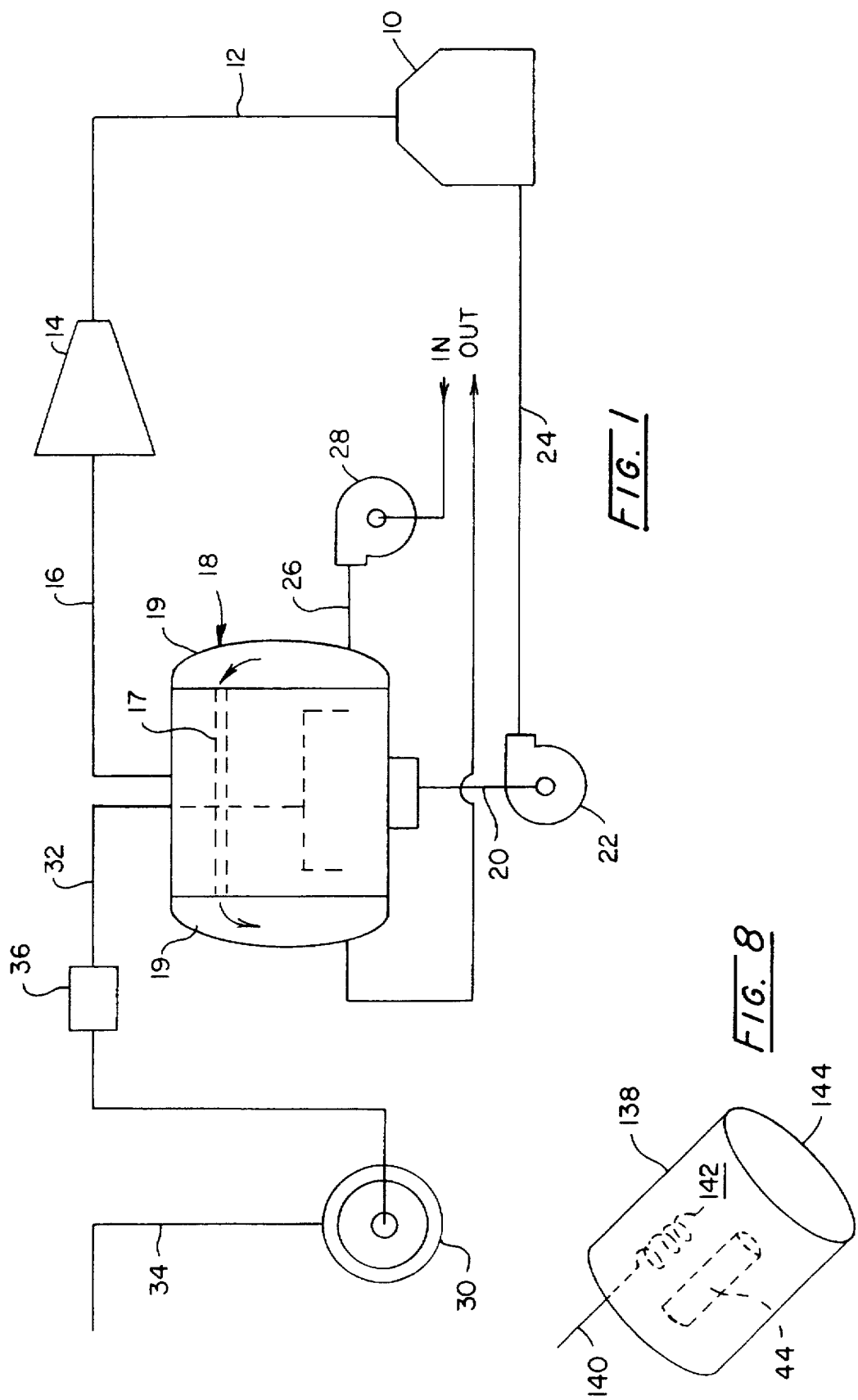
FIG. 1 is a simplified schematic of a steam turbine generator plant where steam is generated to energize a turbine for the generation of electricity.

The drawings will be described in detail in connection with the following description.

DETAILED DESCRIPTION OF THE INVENTION

The apparatus and method for measuring the mass flow rate of the gas component and the mass of the water component of a gas/water vapor source stream flowing in a conduit under reduced pressure are unique for this purpose, but also are unique within a system wherein alarm limits can be set for monitoring the flow conditions within the conduit, sensed conditions beyond normal limits triggering an alarm enabling the operator to effect corrective action. The apparatus of the present invention is seen in simplified schematic form in FIG. 2 and is seen to include temperature and flow sensor 38 which has an output signal carried via line 40 to processor 42 which contains memory and a comparator, water vapor sensor 44 whose output signal in line 46 is connected to processor 42, and pressure sensor 48 whose output signal in line 50 similarly is connected to processor 42. Processor 42 conveniently can be a personal computer, such as a Compaq Portable II computer (Compaq Computer Corp.). Signal line 52 from processor 42 publishes a variety of information which has been gathered from the indicated sensors. For example, from temperature and flow sensor 38 and water vapor sensor 44, which sensors have been properly calibrated in accordance with the precepts of the present invention, air flow rate 54, water vapor density 56, and temperature 60 can be published. Of course, with sensor 48, pressure 58 additionally is known. Since air mass flow rate 54, water vapor density 56, and pressure 58 are known, then water vapor mass flow rate 65 is determinable. Another parameter of interest to the power plant operator is the presentation of the mass ratio of water vapor to air 67, computed by dividing the mass flow rate of water vapor 65 by the mass flow rate of air 54. Finally, a variety of alarm limits can be published such as, for example, low flow flag 62 and high flow flag 64, both conditions being outside the air mass flow rate limits of calibration, to name but two of the variety of alarm limits for which the inventive system has the capability.

The hardware components disclosed herein generate signals that can be processed to derive indicia or parameters (such as described above) of the source stream by a variety of mathematical manipulations and computations. Preferred signal manipulations will be described in detail herein by way of illustration of the present invention and not by way of limitation.

Figure 3:
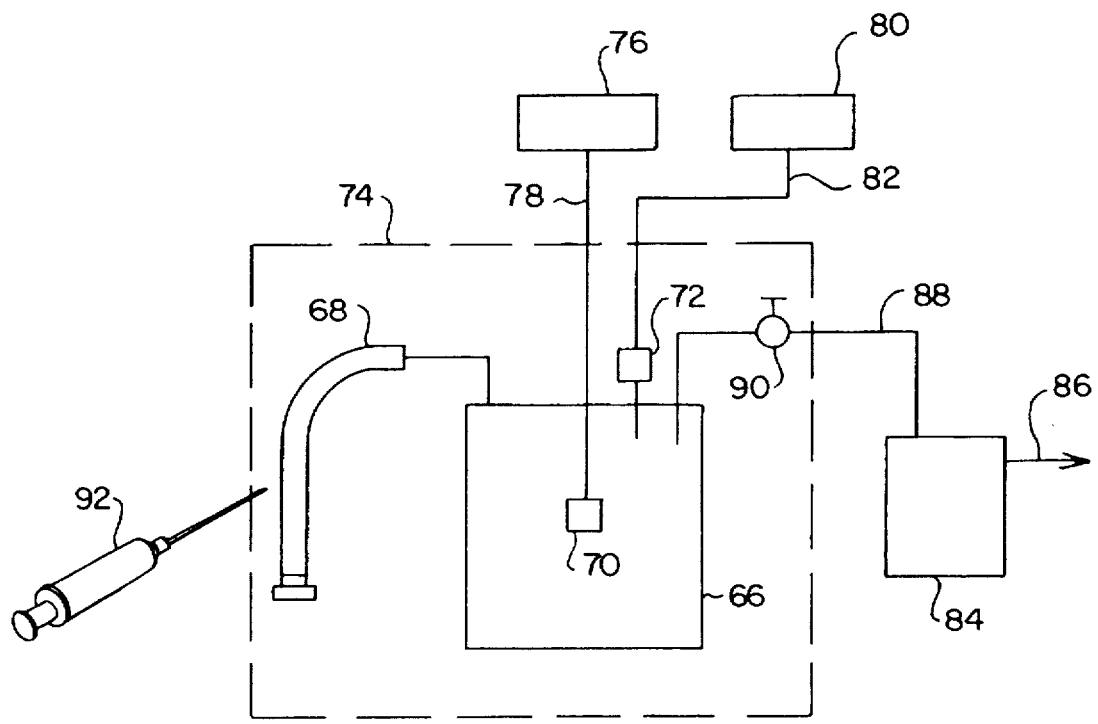
FIG. 3 is a simplified schematic of a water concentration calibration apparatus used to calibrate the output electrical signal of a relative humidity sensor for use in vacuum lines.

As an initial step in the present invention, water vapor sensor 44 (common relative humidity sensors not specifically designed for vacuum applications) needs to be calibrated so that the water content, or relative saturation, can be determined directly from the electrical signal output from water vapor sensor 44. In this regard, reference is made to FIG. 3 wherein the water concentration calibration apparatus is set forth in a simplified schematic drawing. It will be observed that chamber 66 (1000 ml flask), tubing 68, water vapor sensor 70 (Panametrics HybridCap sensor, Panametrics, Inc., Waltham, Mass.) powered by a Kepco PS ATE 150 power supply (Kepco Inc., Flushing, N.Y.), and pressure sensor 72 (Ashcroft K2, Ashcroft, Dresser Industries, Stratford, Conn.) are housed within isothermal tank 74. Read-out 76 is connected via line 78 to water vapor sensor 70 and pressure read-out and power source 80 is connected to pressure sensor 72 via line 82. Vacuum pump 84 (Welch Model No. 1400) with air outlet line 86 is connected via line 88 and valve 90 to chamber 66 for evacuating air from chamber 66 to establish a vacuum. Sensor 72 with associated readout 80 ensures the constancy of the vacuum drawn when valve 90 is closed.

Figure 4:
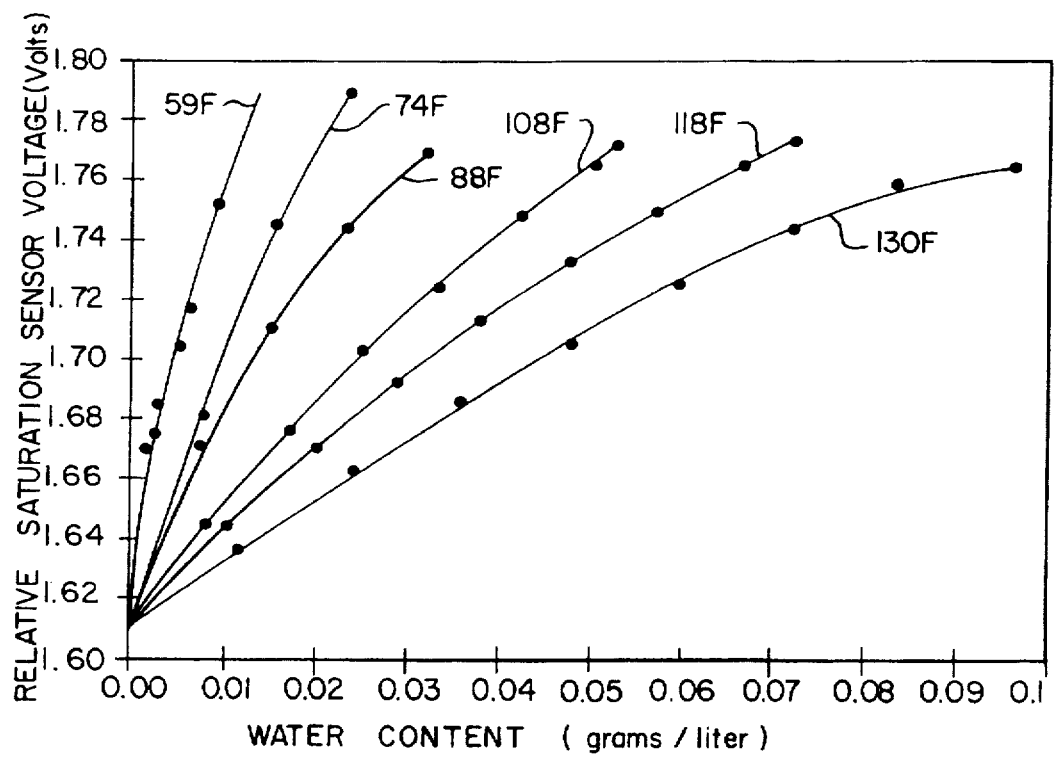
FIG. 4 graphically plots a correlation of the water vapor concentrated voltage of the relative humidity sensor to the water content (expressed in mass per unit volume) as a function of temperature.

Once the vacuum has been established and observed to remain constant by observing readout 80 with valve 90 closed, a known amount of liquid water placed in syringe 92 can be injected into chamber 66 through tubing 68. Because of apparent physisorption by the glass flask and other internal surfaces of water vapor, the amount of water vapor in chamber 66 was determined from the pressure increase (water vapor pressure) by dint of the water injection. Isothermal oven 74 insures a temperature such that only the vapor phase or state of water is permissible within chamber 74 and establishes the temperature at which water vapor saturation density will be computed. At varying temperatures and varying water content established in chamber 66, readings from water vapor sensor 70 were taken and recorded. To insure the water vapor sensor was immune to air partial pressure, the vacuum pressure was varied three times by injecting 50 cc of atmospheric pressure air into chamber 66 through tubing 66 using another syringe. The water vapor readings remaining unchanged. This is so since the volume of the tank and the volume of water therein were constant with the water always being in the vapor state. The signal from sensor 70 in line 78 was recorded as set forth in Table 1 and plotted in FIG. 4 versus water content established in chamber 66 at the various temperatures.

TABLE 1

SATURATION SENSOR CALIBRATION

| Measured Temperature Degrees F. | Measured Water Vapor Pressure in. Hg absolute | Calculated Water Vapor Density lbm/cubic ft. | Water Vapor Saturation Density lbm/cubic ft. | Percent Saturation % | Sensor Output Volts |
|---|---|---|---|---|---|
| 129.7 | 0.0066 | 0.00001 | 0.00628 | 0.1 | 1.620 |
| 111.5 | 0.009 | 0.00001 | 0.00390 | 0.3 | 1.615 |
| 77.8 | 0.007 | 0.00001 | 0.00149 | 0.7 | 1.621 |
| 75.2 | 0.007 | 0.00001 | 0.00137 | 0.8 | 1.619 |
| 69.1 | 0.012 | 0.00002 | 0.00113 | 1.7 | 1.620 |
| 129.2 | 0.449 | 0.00063 | 0.00621 | 10.1 | 1.636 |
| 116.9 | 0.400 | 0.00057 | 0.00451 | 12.7 | 1.645 |
| 104.6 | 0.287 | 0.00042 | 0.00323 | 13.0 | 1.644 |
| 118.0 | 0.629 | 0.00090 | 0.00465 | 19.3 | 1.657 |
| 87.4 | 0.272 | 0.00041 | 0.00198 | 20.7 | 1.6701 |
| 129.3 | 0.985 | 0.00138 | 0.00621 | 22.2 | 1.663 |
| 117.0 | 0.748 | 0.00107 | 0.00453 | 23.6 | 1.670 |
| 104.9 | 0.624 | 0.00091 | 0.00325 | 28.0 | 1.676 |
| 129.2 | 1.304 | 0.00182 | 0.00621 | 29.4 | 1.692 |
| 58.6 | 0.144 | 0.00023 | 0.00077 | 29.5 | 1.684 |
| 73.4 | 0.253 | 0.00039 | 0.00130 | 30.1 | 1.681 |
| 59.0 | 0.156 | 0.00025 | 0.00079 | 31.4 | 1.676 |
| 75.6 | 0.297 | 0.00046 | 0.00139 | 32.9 | 1.697 |

TABLE 1-continued

SATURATION SENSOR CALIBRATION

| Measured Temperature Degrees F. | Measured Water Vapor Pressure in. Hg absolute | Calculated Water Vapor Density lbm/cubic ft. | Water Vapor Saturation Density lbm/cubic ft. | Percent Saturation % | Sensor Output Volts |
|---|---|---|---|---|---|
| 129.3 | 1.469 | 0.00205 | 0.00622 | 33.0 | 1.686 |
| 78.1 | 0.328 | 0.00050 | 0.00150 | 33.5 | 1.689 |
| 116.8 | 1.144 | 0.00163 | 0.00450 | 36.3 | 1.693 |
| 117.9 | 1.275 | 0.00182 | 0.00467 | 39.3 | 1.695 |
| 87.8 | 0.527 | 0.00079 | 0.00200 | 39.7 | 1.710 |
| 105.7 | 0.943 | 0.00137 | 0.00333 | 41.2 | 1.704 |
| 129.6 | 1.964 | 0.00275 | 0.00626 | 43.9 | 1.706 |
| 117.0 | 1.498 | 0.00214 | 0.00452 | 47.3 | 1.714 |
| 106.8 | 1.252 | 0.00182 | 0.00343 | 53.0 | 1.726 |
| 129.7 | 2.442 | 0.00341 | 0.00628 | 54.3 | 1.726 |
| 118.4 | 1.904 | 0.00271 | 0.00470 | 57.7 | 1.725 |
| 117.0 | 1.866 | 0.00267 | 0.00453 | 58.8 | 1.734 |
| 78.4 | 0.621 | 0.00095 | 0.00151 | 62.9 | 1.735 |
| 129.7 | 2.944 | 0.00411 | 0.00629 | 65.4 | 1.745 |
| 88.3 | 0.884 | 0.00133 | 0.00203 | 65.6 | 1.745 |
| 106.7 | 1.552 | 0.00226 | 0.00342 | 65.9 | 1.749 |
| 117.6 | 2.187 | 0.00312 | 0.00460 | 67.9 | 1.751 |
| 129.7 | 3.327 | 0.00465 | 0.00628 | 74.0 | 1.761 |
| 117.9 | 2.461 | 0.00351 | 0.00464 | 75.7 | 1.761 |
| 107.2 | 1.816 | 0.00264 | 0.00347 | 76.2 | 1.766 |
| 117.5 | 2.503 | 0.00357 | 0.00459 | 77.8 | 1.766 |
| 129.8 | 3.696 | 0.00516 | 0.00630 | 82.0 | 1.776 |
| 106.6 | 1.933 | 0.00281 | 0.00342 | 82.3 | 1.773 |
| 88.4 | 1.122 | 0.00169 | 0.00203 | 82.9 | 1.771 |
| 117.3 | 2.659 | 0.00380 | 0.00457 | 83.1 | 1.774 |
| 118.8 | 2.887 | 0.00411 | 0.00475 | 86.5 | 1.779 |
| 117.7 | 3.137 | 0.00448 | 0.00461 | 97.0 | 1.794 |
| 117.1 | 3.208 | 0.00458 | 0.00454 | 100.8 | 1.799 |

Figure 5:
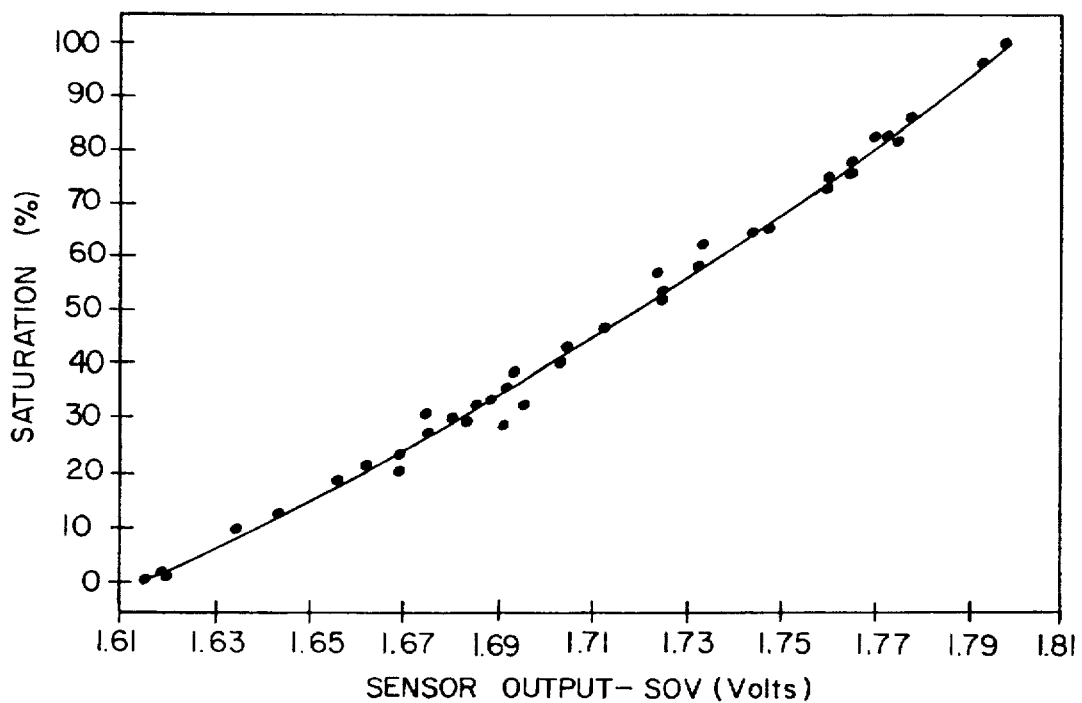
FIG. 5 is a graphical plot of the normalized water vapor concentration voltage of the relative humidity sensor versus relative saturation as calculated from the results displayed in FIG. 4.

The water vapor saturation density was obtained from tables "properties of saturated steam" found in any textbook for the temperature being measured (e.g., Handbook of Chemistry and Physics, 47th edition, page E-11 et seq., The Chemical Rubber Company, 1966; and Perry, et al., Chemical Engineers' Handbook, Fifth Edition, McGraw-Hill Book Company, 1973), the disclosures of which are expressly incorporated herein by reference. Such tables also can include, for example, water vapor partial pressure, specific volume, enthalpy, and entropy data at various temperatures. Note the data of Table 1 is ordered for increasing percent saturation. The data for all temperature calibration runs presented in Table 1 is plotted graphically in FIG. 5 showing percent saturation versus sensor output voltage. The curve is nearly identical to what might be expected at atmospheric pressure for the same sensor and shows this device is suitable for vacuum applications. With the calibration of water vapor sensor 70 complete, electrical signals from it can be directly converted into relative saturation values which can be stored in memory in processor 42 which additionally can be programmed for interpolation for values not in storage or an algorithm can be employed. It should be noted that additional common relative humidity sensors (not designed for vacuum operation) were calibrated under vacuum with similar results. These sensors included a Mini-Cap 2 (Panametrics, Inc.), an EMD-2000 (Phys-Chem Scientific Corp.), and a Series 691 (Philips Components, Inc.). Thus, it appears that commercial relative humidity sensors do function under vacuum. Assuming reproducibility of readings of various models of sensors, calibration of each relative humidity sensor should not be necessary, but for, perhaps, a single test point for each unit to be run to confirm this assumption. It should be understood, however, that relative humidity sensors specially designed for operation in vacuum could be used to advantage in the present invention and the calibration scheme set forth herein would probably not be necessary.

Figure 2:
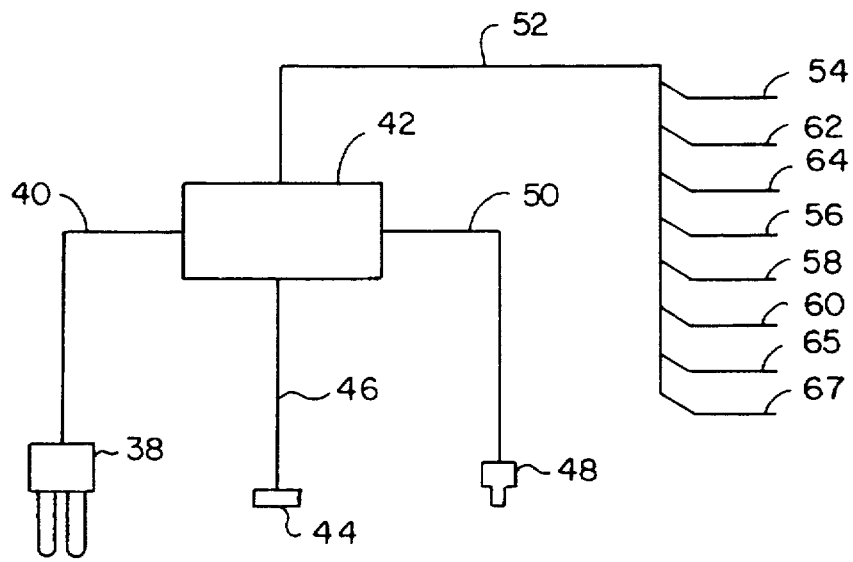
FIG. 2 is a simplified schematic representation of the components used in forming the novel apparatus which measures the mass of gas and water vapor components of the gas/water vapor stream.
Figure 6:
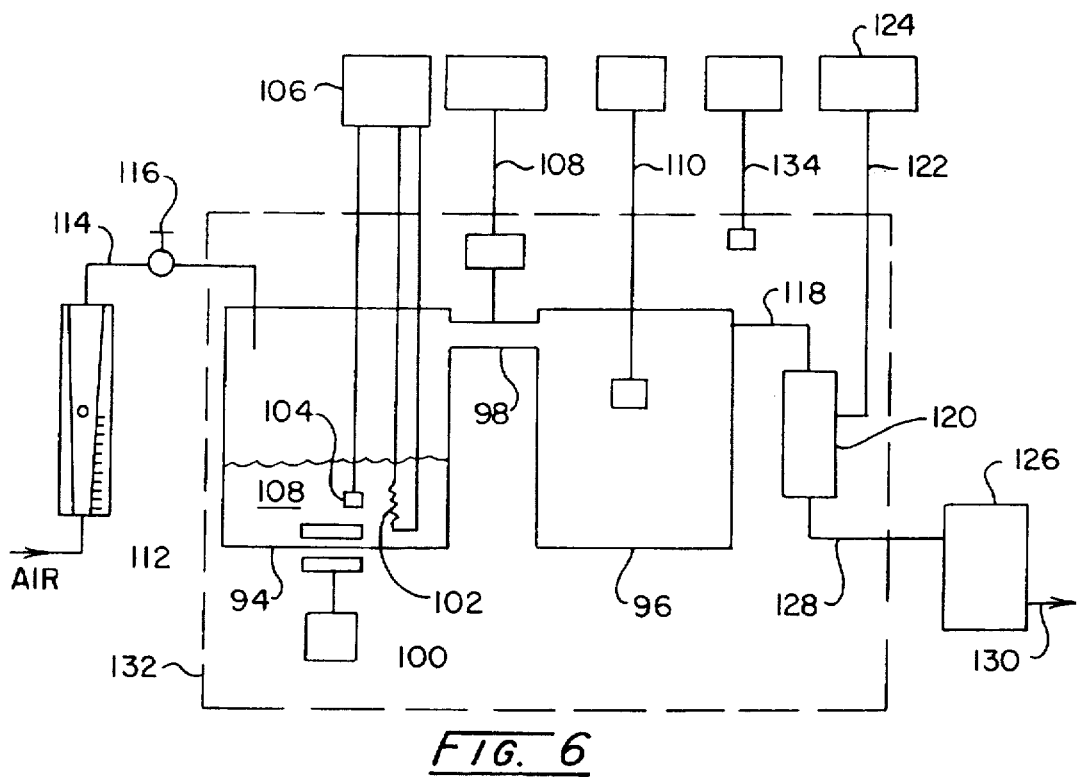
FIG. 6 is a schematic of the air flow measurement configuration used to correlate the flow rate of the gas component of a flowing gas/water vapor reference stream and the output electrical signal of a temperature-compensated flow sensor as a function of temperature and water vapor concentration.

Next, flow sensor 38 in FIG. 2 can be calibrated similarly using the equipment configuration depicted in FIG. 6. Chambers 94 and 96 (250 ml flasks) in FIG. 6 are connected by line 98. Chamber 94 is fitted with magnetic stirrer assembly 100 (model 120M stirrer, Fisher Scientific Corp.), heater 102 and temperature sensor 104 which are connected to temperature controller 106. Water 108 is housed in chamber 94. Line 98 is fitted with pressure sensor assembly 108 while chamber 96 is fitted with water vapor sensor assembly 110. Air is metered through variable arc flow meter 112 (Model F1-1805, Omega Engineering, Inc.) and passed into chamber 94 via line 114 which is fitted with valve 116 suitable for adjusting air flow. Air/water vapor mixture is withdrawn from chamber 94 through chamber 96 via line 118 and passed through flow meter 120 (Rheotherm LFl-100-TU1/8 flow instrument, Intek, Inc., Westerville, Ohio). The electrical signal from flow meter 120 passes via line 122 into readout 124. Vacuum pump 126 (Model 1400, Welch Co.) provides the motive force for the air and air/water vapor flows via line 128 which is connected to flow meter 120 and thence exhausted through line 130. Isothermal chamber 132 was used to maintain the external temperature of chambers 94 and 96 with temperature sensor assembly 134 providing the readout of such temperature.

In order to compensate for temperature variations of the air flow through flow meter 120, air only runs (no water in chamber 94) were conducted at 70° and 117° F. and the output signals recorded as set forth in Table 2 below.

TABLE 2

| Air Flow Rate Standard CC per min (SCCM) | Output Signal | | | Signal Difference due to Temperature (Measured Signals) mV |
|---|---|---|---|---|
| | 70° F. Measured Signal Volts | 117° F. Ambient | | |
| | | Measured Signal Volts | Temperature Compensated Signal Volts | |
| 1872 | 7.211 | 7.041 | 7.253 | 170 |
| 1713 | 7.332 | 7.148 | 7.360 | 184 |
| 1516 | 7.470 | 7.258 | 7.470 | 212 |
| 1323 | 7.593 | 7.388 | 7.600 | 205 |
| 1143 | 7.740 | 7.542 | 7.754 | 198 |
| 967.6 | 7.928 | 7.729 | 7.941 | 199 |
| 799.8 | 8.180 | 7.983 | 8.195 | 197 |
| 568.4 | 8.554 | 8.315 | 8.527 | 239 |
| 338.3 | 9.060 | 8.808 | 9.020 | 252 |
| 116.0 | 9.978 | 9.702 | 9.914 | 276 |
| Average Signal Difference (mV) | | | | 213 |
| Temperature Compensation (mV/°F.) 70° F. Reference | | | | 4.5 |

These data demonstrate that an error correction of about 213/(117-70) or 4.5 mV/°F. can be applied to the hot air signals in order to provide all signals normalized to about room temperature, thus eliminating temperature effects experienced by flow meter 120.

Using the equipment configuration in FIG. 6, known air flow rates were admitted into the system at various water vapor concentrations in chamber 96 (as determined from calibrated water vapor sensor assembly 110) at various temperatures. The data recorded is set forth in Table 3 below.

A determination of the water vapor flow rate in the conduit can be obtained by multiplying the water vapor density by the velocity of the flowing gas (air)/water vapor mixture and by the cross-sectional area of the conduit (which area was previously determined and entered into memory). The water vapor density is derived from the measured temperature and relative water vapor saturation, as described above. The velocity of the stream is determined by dividing the derived air flow rate (e.g., in units of SCFM) by the cross-sectional are of the conduit and multiplying by the

TABLE 3

FLOW RATE vs. WATER VAPOR DENSITY

| Dry Air Flow Rate SCCM | 65° F. Ambient | | | 98° F. Ambient | | | 112° F. Ambient | | |
|---|---|---|---|---|---|---|---|---|---|
| | Temperature Compensated Flow Signal Volts | Relative Saturation % | Water Vapor Density Lbm/Cu. ft. | Temperature Compensated Flow Signal Volts | Relative Saturation % | Water Vapor Density Lbm/Cu. ft. | Temperature Compensated Flow Signal Volts | Relative Saturation % | Water Vapor Density Lbm/Cu. ft |
| 1872 | 7.095 | 75.8 | .000747 | 6.918 | 57.3 | .00115 | 6.519 | 63.9 | .00253 |
| 1323 | 7.399 | 75.2 | .000742 | | | | | | |
| 1143 | | | | 7.303 | 58.4 | .00117 | 6.826 | 56.9 | .00225 |
| 967.6 | 7.682 | 76.9 | .000759 | | | | | | |
| 779.8 | | | | 7.612 | 58.9 | .00118 | 7.033 | 60.4 | .00239 |
| 568.4 | 8.204 | 82.7 | .000816 | 8.125 | 59.8 | .00120 | | | |
| 338.3 | 8.613 | 83.1 | .000820 | 8.125 | 60.2 | .00120 | 7.294 | 61.1 | .00242 |
| 225.2 | | | | 8.333 | 60.2 | .00121 | | | |
| 125.6 | | | | | | | 7.475 | 61.2 | .00242 |
| 116 | 9.293 | 85.4 | .000842 | 8.522 | 61.9 | .00124 | | | |
| 67.1 | | | | 8.616 | 61.9 | .00124 | | | |
| 42.0 | 9.563 | 82.5 | .000814 | 8.650 | 62.7 | .00126 | 7.566 | 60.8 | .00241 |
| Average Water Vapor Density (Lbm/Cu. ft.) = .000791 | | | | Average Water Vapor Density (Lbm/Cu. ft.) = .00121 | | | Average Water Vapor Density (Lbm/Cu. ft.) = .00240 | | |

Figure 7:
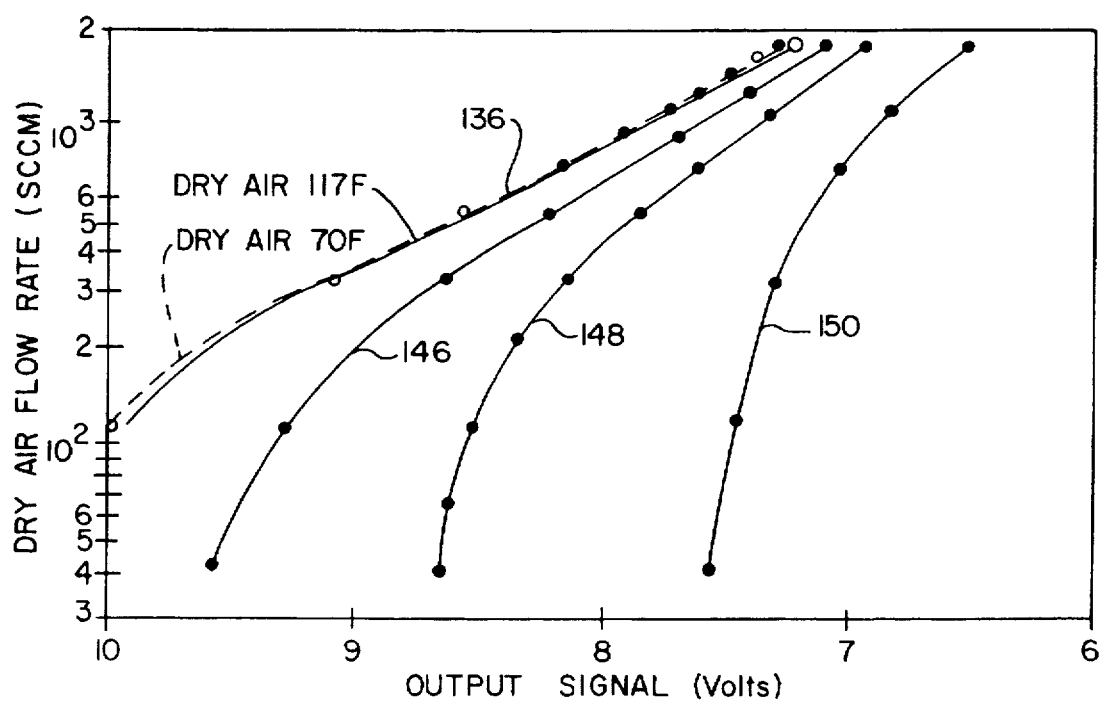
FIG. 7 is a graphic plot of the data generated using the apparatus in FIG. 6 where volumetric air flow is plotted versus output voltage of the temperature-compensated flow sensor at various water vapor concentrations.

The above-tabulated data also is depicted graphically in FIG. 7. Note, that the air only calibration results represented by line 136 at two temperatures, 70° and 117° F. also is shown. Line 146 corresponds to a water vapor density in air of about 0.0008 lbs/ft$^3$; and lines 148 and 150 correspond, respectively, to an average value of 0.0012 and 0.0024 lb/ft$^3$, respectively. Again, these data can be stored in memory in processor 42. Alternatively, one could generate an empirical formula to model the data in Table 3 and FIG. 7 and use such formula to determine the air mass flow rate and mass of water vapor flowing in a conduit using the signals from the water vapor sensor temperature sensor and the flow sensor.

ratio of the standard or normal atmospheric pressure of 29.9 inches Hg absolute divided by the stream air partial pressure. The stream air partial pressure can be found by subtracting the water vapor partial pressure from the measured total pressure derived from the output signal of the pressure sensor. The water vapor partial pressure is found from the stored correlation of saturated water vapor density and water vapor partial pressure as a function of stream temperature using the determined water vapor density.

Another important parameter to be determined is the water vapor mass to air mass ratio. To derive this ratio the processor is instructed to divide the water mass flow rate by the air mass flow rate and display the result. Since the air mass flow rate is displayed in units of SCFM, the conversion to lbs/minute simply is performed by multiplying SCFM by the density of dry air at standard conditions which has been stored in memory.

As to appropriate flow sensors for use in the inventive apparatus, virtually any flow sensor (or flow meter) can be used from simple flow restriction or orifice flow sensors to sophisticated microprocessor-based flow meters. The preferred flow sensor is disclosed in U.S. Pat. No. 4,255,968, the disclosure of which is expressly incorporated herein by reference. The flow sensor of choice desirably has been "temperature-compensated" (such as described above) or is "temperature independent".

It is entirely conceivable that the water vapor in conduit 32 (FIG. 1) subjected to measurement could be over 100% (supersaturated) or contain a water mist due to a variety of reasons. Thus, appropriate water vapor sensor 44 (FIG. 2) should be capable of operating near 100% relative humidity, such as a Phys-Chem EMD-2000 micro relative humidity sensor (Phys-Chem Scientific Corp., New York, N.Y.). As to reasons for this condition, line 32 may be located in an environment where the ambient temperature is below the cooling water temperature of condenser 18. Also, should the extraction suction line shroud surrounding a section of cooling tubes within condenser 18 develop openings or otherwise not be properly sealed, steam can enter the line directly without passing over the cooling tubes.

When steam mist in present in line 32, water vapor sensor 44 would be saturated and unable to provide an output in relation to water content. Referring to FIG. 8, water vapor sensor 44 is housed within residence chamber 138 which provides temperature control by heater 140 so that the temperature is greater than in line 32 by some amount, say up to 5° F. Space 142 optionally may be packed or a screen may surmount aperture 144 to "demist" the air entering chamber 138. Since relative humidity decreases by about 3% for each 1° F. increase in temperature, the air within chamber 138 would be "dried" by heater 140 permitting a measurement of the water vapor concentration at the higher temperature, resulting in a determination of the higher water content. The higher indicated water vapor content at the flow sensor then would be used to correct the flow sensor reading of the flow sensor to obtain the air flow rate, computed water vapor density, and water to air mass ratio. If the water vapor sensor cannot effect a reading with the chosen 5° F. temperature excursion, then an alarm should be activated as a steam, leak or other failure mode may be indicated.

Alternative, if a mist detector were used when mist was present, there might not be a need to measure water vapor density with the relative saturation sensor. The water vapor concentration (density) would be at the value of saturation determined from temperature and the "steam table" correlation.

When steam mist is present in line 32 as described above, the configuration for the relative saturation sensor of FIG. 8 could permit its output signal to no longer be saturated but not be indicative of the water mist content. Mist for some flow sensors could cause a signal variation above that defined for water vapor content. In this case, measurement of the water mist content would be useful for the purpose of correcting the flow sensor signal in a manner described above using the relative saturation sensor for water vapor content.

An example of such a sensor would be an optical device where a light beam would undergo scattering or otherwise be attenuated in relation to water mist content similar to clouds in the sky. A light intensity sensor output signal would be calibrated as a function of mist density and used to correct the flow signal of mist sensitive gas/water vapor flow sensors. Another method can be visualized where a heated surface exposed to the mist containing steam and another turned away from direct impact of the steam could be utilized. The temperature differential between the two surfaces would be a measure of the mist content due to the cooling effect of the impacting water droplets. This method would be similar to sensing methods disclosed in U.S. Pat. No. 4,255,968 but employed for a different purpose.

Other alarm limits can be set, for example, based on loss of vacuum as measured by the pressure sensor indicative of loss of pump efficiency or a leak in the pumping system, unexpectedly high temperature with high pressure which may indicate condenser binding, unexpectedly low temperature with high pressure and saturated water vapor which also may indicate condenser binding, and the like.

Finally, should the water vapor sensor fail, the efficiency of the condenser can be assumed to be high and the gas/water vapor stream temperature can be assumed to be the same as the condenser tube temperature at the stream conduit shroud interface. With these assumptions, along with the measured total pressure for the stream a determination of the partial pressure of the water vapor, and hence its mass density could be calculated.

It will be appreciated that a wide variety of combinations of operating parameters can be envisioned for the inventive apparatus, especially when the capabilities of a computer are incorporated into the design. The description herein is by way of illustration and not by way of limitation. All citations referred to herein are expressly incorporated herein by reference.

I claim:

1. Method for measuring the flow rate of the gas component and the mass density of water vapor component of a gas/water vapor source stream flowing in a conduit under reduced pressure, which comprises the steps of:

(a) storing a correlation of relative saturation of water vapor in said gas and the output electrical signal of a relative humidity sensor;

(b) storing a correlation of the flow rate of the gas component of a flowing gas/water vapor reference stream and the output electrical signal of a temperature-compensated flow sensor as a function of water vapor density;

(c) storing a correlation of maximum water vapor saturation in the gas as a function of temperature;

(d) generating an electrical signal of a temperature sensor in contact with said source stream;

(e) generating an output electrical signal of a relative humidity sensor in contact with said source stream;

(f) generating an output electrical signal of a temperature-compensated flow sensor in contact with said source stream;

(g) comparing said signal (e) with said stored correlation (a) to derive a relative saturation value which value is multiplied by the maximum water vapor saturation correlation (c) for the temperature determined from signal (d) in order to derive the mass density of the water vapor component of said source stream; and (h) comparing said signal (f) with said stored correlation (b) at derived water vapor mass density (g) to derive the flow rate of the gas component of said source stream.

2. The method of claim 1, wherein said relative humidity sensor is calibrated by the steps of:

(a1) in a gas/water vapor mixture held under sub-atmospheric pressure, fixing the water vapor concentration at varying values up to saturation and recording the electrical signal from said relative humidity sensor which signal corresponds thereto;

(a2) at each temperature, dividing the water vapor concentration from step (a1) by the saturation value of step (c) to generate the relative saturation of water vapor; and (a3) correlating the electrical signal of said relative humidity sensor to the relative saturation under sub-atmospheric pressure generated in step (a2).

3. The method of claim 1, wherein said conduit is a vacuum suction line from a condenser which receives steam from a steam turbine.

4. The method of claim 1, wherein said gas is air.

5. The method of claim 1, which includes the step of:

(i) generating an output signal of a pressure sensor in contact with the source stream in said conduit.

6. The method of claim 5, wherein the water vapor mass flow rate in the conduit is determined by the steps of:

(j1) storing the cross-sectional area of the conduit;

(j2) storing the partial pressure of water vapor as a function of water vapor density;

(j3) storing the standard atmospheric pressure of said gas;

(j4) determining the partial pressure of the gas component by subtracting the stored water vapor partial pressure (j2) at the water vapor density derived in (g) from total pressure signal (i);

(j5) determining the source stream rate by dividing the stream flow rate from step (h) by the stored area (j1), and then multiplying by the ratio of standard atmospheric pressure (j3) divided by the gas partial pressure in step (j4); and (j6) determining the water vapor flow rate by multiplying the mass density of water vapor derived in step (g) by the stream rate determined in step (j5) and by the stored area (j1).

7. The method of claim 6, wherein a measured pressure above an alarm limit triggers an alarm indicative thereof.

8. The method of claim 6, which includes the steps of:

(k) storing the density of air at standard conditions;

(l) multiplying the stored density of air (k) by the air flow rate (h) in units of SCFM to derive the mass flow rate of air; and (m) dividing the mass flow rate of water vapor (j6) by the mass flow rate of air (h) to determine the mass ratio of water vapor to air.

9. Apparatus for measuring the flow rate of the gas component and the mass density of the water vapor component of a gas/water vapor source stream flowing in a conduit under sub-atmospheric pressure, which comprises:

(a) memory in which is stored the correlation of relative saturation of water vapor in said gas and the output electrical signal of a relative humidity sensor;

(b) memory in which is stored the correlation of the flow rate of the gas component of a flowing gas/water vapor reference stream and the output electrical signal of a temperature-compensated flow sensor as a function of water vapor density;

(c) memory in which is stored a correlation of maximum water vapor saturation in the gas as a function of temperature;

(d) a temperature sensor in thermal contact with the source stream which generates an electrical signal representative of the temperature of said source stream;

(e) a relative humidity sensor in contact with said source stream which generates an electrical signal representative of the relative saturation in said source stream;

(f) a temperature-compensated flow sensor in contact with said source stream which generates an electrical signal representative of the flow rate of said source stream;

(g) a comparator which compares the signal from relative humidity sensor (e) with said stored correlation in memory (a) to derive a relative saturation value which value is multiplied by the maximum water vapor saturation correlation in memory (c) for the temperature determined from temperature sensor (d) in order to derive the mass density of the water vapor component of said source stream; and (h) a comparator which compares the electrical signal from flow sensor (f) with said stored correlation in memory (b) to derive the flow rate of the gas component of said source stream.

10. The apparatus of claim 9, which additionally comprises:

(i) a pressure sensor in contact with the source stream in said conduit for generating an electrical signal representative of the pressure of the source stream in said conduit.

11. The apparatus of claim 10, wherein additionally comprises:

(j) memory in which is stored the cross-sectional area of the conduit;

(k) memory in which is stored standard atmospheric pressure of said gas;

(l) memory in which is stored the partial pressures of water vapor as a function of water vapor density;

(m) calculator for:

(1) subtracting the stored water vapor partial pressure from memory (l) from total pressure measured in (i) for determining the partial pressure of the gas component;

(2) dividing the stream flow rate from comparator (h) by the cross-sectional area in memory (j), and then multiplying by the ratio of standard atmospheric pressure in memory (k) divided by the gas partial pressure determined in (m1) for determining the source stream rate; and (3) multiplying the mass density of water vapor derived in comparator (g) by the stream rate determined in (m2) and by the stored cross-sectional area in memory (j) for determining the water vapor flow rate.

12. The apparatus of claim 10, which additionally comprises:

(m) memory in which is stored a pressure alarm limit;

(n) a comparator that compares the signal from pressure sensor (i) with the stored alarm limit; and (o) an alarm that is activated when comparator (n) determines that the signal from pressure sensor (i) is greater than the stored alarm limit.

\* \* \* \* \*